United States Patent [19]

Hjerten

[11] Patent Number: 4,906,344

[45] Date of Patent: Mar. 6, 1990

[54] THERMAL TECHNIQUE FOR BULK FLUID MOVEMENT IN CAPILLARY ELECTROPHORESIS

[75] Inventor: Stellan Hjerten, Uppsala, Sweden

[73] Assignee: Bio-Rad Laboratories, Inc., Hercules, Calif.

[21] Appl. No.: 370,368

[22] Filed: Jun. 22, 1989

[51] Int. Cl.⁴ .................. G01N 27/26; B01D 57/02
[52] U.S. Cl. ..................... 264/182.8; 304/299 R; 304/180.1; 304/183.3
[58] Field of Search ............. 204/299 R, 183.3, 180.1, 204/182.8

[56] References Cited

U.S. PATENT DOCUMENTS 3,932,264  1/1976  Haruki et al. ................ 204/183.3 X
4,676,897  6/1987  Kuzé et al. .................. 204/183.3 X

FOREIGN PATENT DOCUMENTS 56-119842   9/1981  Japan ............................. 204/299 R
58-168957  10/1983  Japan ............................. 204/299 R
59-182355  10/1984  Japan ............................. 204/299 R
60-138447   7/1985  Japan ............................. 204/180.1
60-138450   7/1985  Japan ............................. 204/183.3

OTHER PUBLICATIONS

Smith, R. D. et al. "Sample introduction and separation in capillary electrophoresis and combination with mass spectrometric detection" *Talanta*, 36(1-2) pp. 161-169 (1989).

Verheggen, T. P. et al. "Simple sampling device for capillary isotachophoresis and capillary zone electrophoresis" *Journal of Chromatography*, 452, pp. 615-622 (1988).

Rose, D. J. et al. "Characterization and automation of sample introduction methods for capillary zone electrophoresis" *Analytical Chemistry*, 60(7), pp. 642-8 (1988).

Huang, X. et al. "Bias in quantitative capillary zone electrophoresis caused by electrokinetic sample injection" *Analytical Chemistry* 60(4) pp. 375-377 (1988).

Honda, S. et al "Evaluation of an automatic siphonic sampler for capillary zone electrophoresis" *Journal of Chromatography*, 404(2), pp. 313-320 (1987).

Wallingford, R. A. et al. "Characterization of a microinjector for capillary zone electrophoresis" Analytical Chemistry, 59(4), pp. 678-681 (1987).

Lukacs, K. D. et al. "Capillary zone electrophoresis: effect of physical parameter on separation efficiency and quantitation" J. High Resolution. Chromatogr. Chromatogr. Commun. 8(8) pp. 407-411 (1985).

*Primary Examiner*—John F. Niebling
*Assistant Examiner*—John S. Starsiak, Jr.
*Attorney, Agent, or Firm*—Townsend and Townsend

[57] ABSTRACT

Bulk fluid movement in a capillary electrophoresis system is achieved by imposing a temperature change on either a portion of the capillary or a bulb joined to the capillary at one end. The process may be used for sample loading, in which case a small volume introduction is made, or for flushing of the capillary with buffer solution, in which a larger volume introduction is made. The temperature change may be either an increase or a decrease, and the volume passed into or through the capillary is controlled to a high degree of precision by selection and accurate measurement of the volume of the bulb or capillary portion to which the temperature change is applied together with accurate control of the temperature change itself.

25 Claims, 4 Drawing Sheets

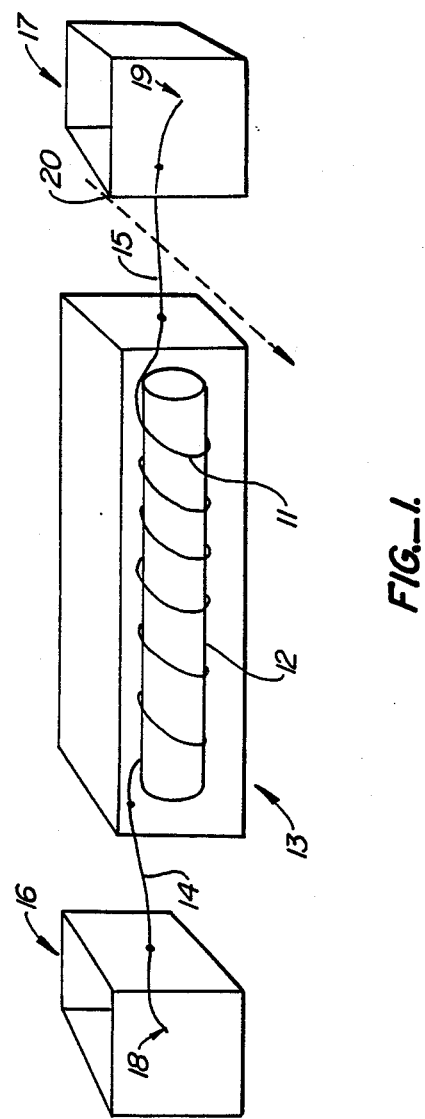
FIG._1.

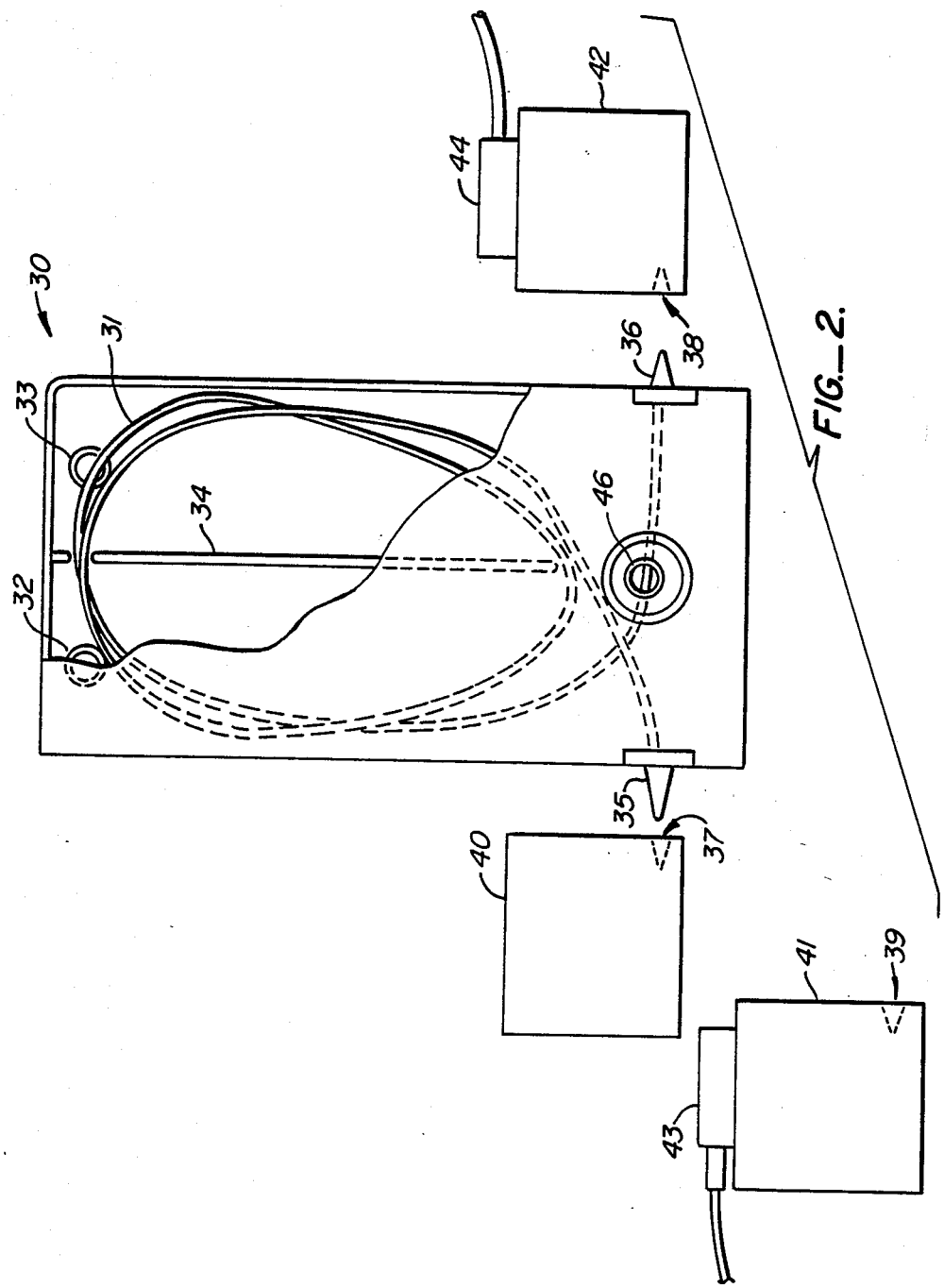

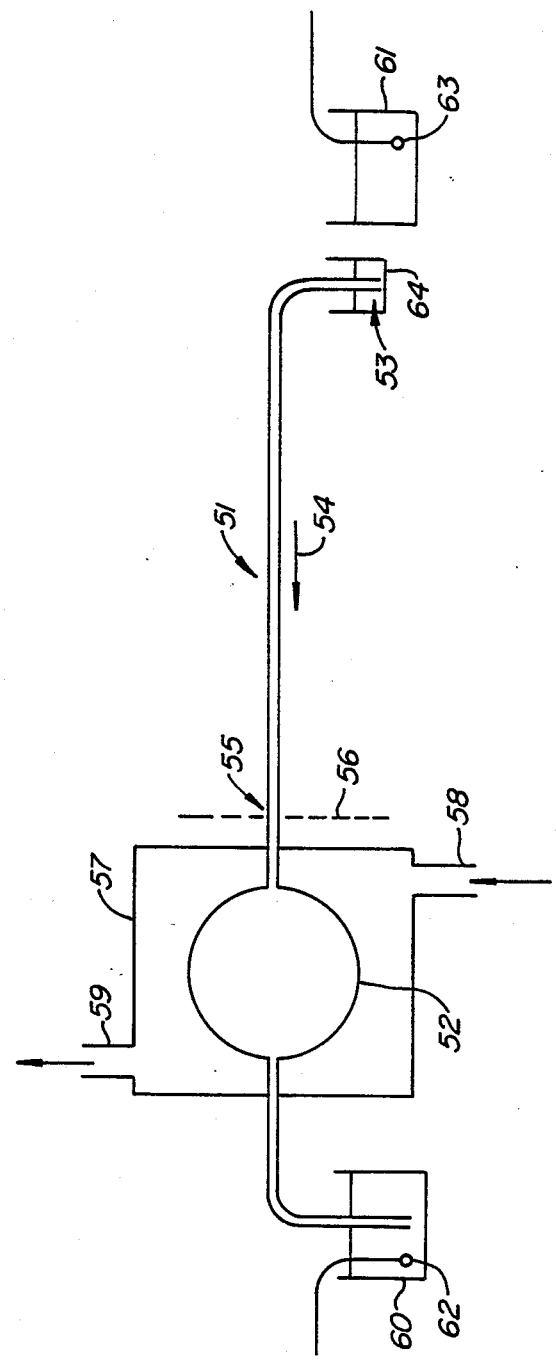
FIG._3.

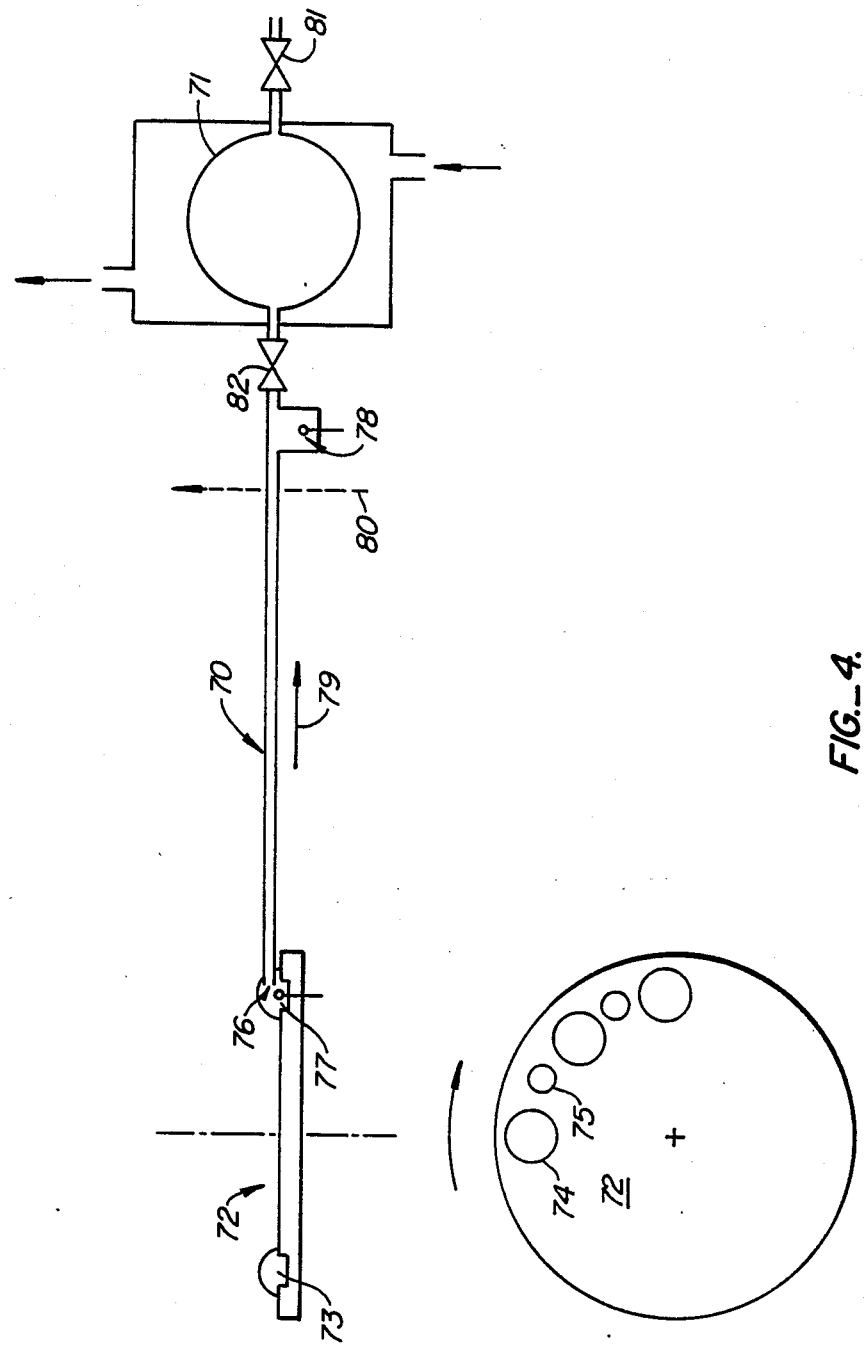
FIG._4.

THERMAL TECHNIQUE FOR BULK FLUID MOVEMENT IN CAPILLARY ELECTROPHORESIS

This invention relates to capillary electrophoresis. and in particular to methods of moving fluids in rapid bulk flow either into or through a capillary electrophoresis column, with primary emphasis on sample loading.

BACKGROUND AND SUMMARY OF THE INVENTION

Capillary electrophoresis is a technique of considerable interest in the analysis of biological mixtures, particularly mixtures of small peptides proteins and nucleic acids, since it can be used on extremely small samples and permits the use of high voltages, thereby achieving separations at high speed.

One of the problems with capillary electrophoresis is the loading of the sample, i.e., its placement inside the end of the capillary in preparation for the separation. At present, this is commonly achieved by electrophoretic. electroendosmotic or pressure differential techniques.

In electrophoretic loading, a high voltage is used over a short period of time to transfer the sample from a sample reservoir into the capillary. The goal is to move small amounts of all species in the sample a short distance into the capillary. Once this is done, the sample reservoir is replaced with an appropriate buffer solution to permit one to proceed with electrophoretic separation of the loaded species.

What actually occurs in electroendosmotic loading is a combination of electrophoresis and electroendosmosis, with electroendosmosis having the predominating effect. The electroendosmosis varies from one experiment to the next, however, causing difficulties in the reproducibility of the sample volume.

Electroendosmosis can be suppressed by the application of appropriate coatings to the inside of the capillary tube, leaving electrophoresis as the sole driving force for the sample injection. Electrophoresis, however, has its own disadvantages. These arise from the differentials which necessarily exist among the various species in the sample in terms of their response to the electric potential. These differentials affect the distance which the species travel into the capillary during loading and thus the amounts of each species entering the capillary. Slowly migrating substances will thus migrate a shorter distance into the tube than will the faster migrating substances. Depending on the loading conditions, therefore, the composition of the applied sample may differ from that of the original sample.

Other variables in electrophoresis such as fluctuations in current strength may also enter into consideration. The significance and importance of these variables may vary.

In hydraulic loading, sample introduction is achieved by a pressure differential across the capillary either by applying a partial vacuum to the outlet end or a positive pressure to the inlet end. Problems with hydraulic loading arise from the limited extent to which one can control the pressure differential and its duration, two critical parameters which together govern the volume of the sample introduced.

It has now been discovered that bulk liquid flow may be achieved in a capillary tube in an electrophoretic system to a highly precise and reproducible degree, by imposing a controlled temperature change on the contents of either the tube or a closed vessel in fluid communication with the tube. The discovery is applicable to small volume introductions into the tube for purposes such as loading sample, as well as large volume transfers into or through the tube for purposes such as flushing the tube with buffer.

The temperature change may be a drop in temperature or a rise, and may occur between any initial and final temperature which will result in a controlled thermal contraction or expansion. Temperatures which do not involve a phase change of the heated or cooled medium, and thus bring about a continuous volume change will be preferred. In cases where the temperature change is imposed on the capillary tube itself, the temperatures will most conveniently be selected such that the final temperature is the temperature at which the separation is to be performed.

Thus, certain embodiments of the invention involve imposing a temperature change on the capillary itself. These embodiments are most useful in loading the capillary with a sample. In these embodiments, the capillary is filled with separation medium, and the temperature of the filled capillary is adjusted as necessary to prepare for a temperature drop of a magnitude calculated to achieve a selected volume contraction. The magnitude of the temperature drop is of course determined in conjunction with the length of capillary to which the temperature drop is applied, and this length may be either the entire capillary or a selected portion of its length.

Once the capillary temperature is equilibrated at the initial temperature, the end of the capillary in which the sample is to be introduced is submerged in a reservoir containing the sample. The temperature of the capillary or its temperature-controlled portion is then lowered to the final temperature, causing an aliquot of the sample is drawn into the capillary end. The final temperature is then maintained as the reservoir is replaced with an electrode buffer, and electrophoresis is performed. Appropriate and accurate selection of both the length of the capillary undergoing the temperature change and the magnitude of the temperature change will permit accurate and highly reproducible control of the size of the aliquot with no change in the proportion of the sample components as they enter the capillary.

In other embodiments of the invention, the temperature change is imposed on a bulb or other external vessel filled with liquid and joined to one end of the capillary in full fluid communication with the capillary contents. This permits the bulk fluid movement to occur without imposing any temperature change on the capillary itself. Depending on its location, the bulb may either push or pull liquid through the capillary, and may do so either directly or through intervening reservoirs. The temperature change may thus be either a rise or a drop. The use of a bulb also offers a wider range of volumetric flow since it is not limited to the dimensions of the capillary. When the volume of the bulb is large relative to the capillary volume sample loading may be achieved with a very small change in temperature. A bulb is particularly useful, however, in flushing the entire capillary with buffer.

Bulk fluid movement by either of these methods, whether it be loading of sample or flushing of the entire capillary, can be done with the same degree of precision as a thermometer. Further advantages, features and embodiments of the invention will be apparent from the description which follows.

BRIEF DESCRIPTION OF THE DRAWINGS

FIG. 1 is a diagrammatic representation of a generalized approach to the invention in which the temperature change is applied to the capillary itself.

FIG. 2 is an illustration of a particular embodiment of the invention utilizing the principles of FIG. 1. shown in partial cutaway.

FIG. 3 is a diagrammatic representation of a system in accordance with the invention in which the temperature change is applied to a bulb external to the separatory portion of the capillary.

FIG. 4 is a diagrammatic representation of an automated system in accordance with the invention, also utilizing a temperature-controlled bulb.

DETAILED DESCRIPTION OF THE INVENTION AND PREFERRED EMBODIMENTS

This invention is functional with a wide variety of electrophoretic separation media. Any medium may be used which can be placed inside a capillary tube and which is capable either of contracting or expanding upon a temperature change or of being drawn a distance through the tube by a medium contracting or expanding in a vessel adjoined to the tube, depending on the particular embodiment. Possibilities extend to both gels and solutions, generally aqueous, the solutions including polymer solutions of elevated viscosity as well as simple buffer solutions. Aqueous buffer solutions are preferred.

The following discussion will begin with those embodiments in which the temperature change is imposed on the capillary itself, to be followed by embodiments in which the temperature change is imposed on a bulb external to the capillary but in fluid communication with the capillary interior.

For those embodiments in which the capillary temperature is varied, the size of the capillary in terms of both diameter and length is not critical and can vary widely. In most cases, capillaries having inner diameters of about 10 to about 200 microns will be used, preferably, those with inner diameters of about 20 to about 100 microns. The entire capillary may be temperature controlled to achieve the transfer. In most cases, however, it will be more convenient to impose the temperature change on only a portion of the capillary, due to the need for fluid-tight connections at the capillary ends. For capillaries where on-line detection is used, the detection point may be either in a temperature-controlled section of the capillary or downstream of the temperature controlled section.

The length of the temperature-controlled section may vary widely, depending on the desired aliquot size and the preferred range of temperature differential, as well as the coefficient of thermal expansion of the separation medium. In most cases, best results will be achieved with temperature-controlled lengths of about 50 mm to about 2000 mm, preferably about 100 mm to about 1000 mm.

Sample aliquots of a wide range of volumes may be loaded by this technique. It is contemplated that most separations to which this invention will be applied will involve aliquots ranging from about 0.0003 to about 0.03 μL, preferably about 0.0005 to about 0.005 μL, in volume. For a capillary having an internal diameter of 0.05 mm. aliquots within these ranges would extend into the capillary to distances of about 0.15 to about 15 mm. preferable 0.25 to about 2.5 mm.

The required temperature change is readily calculated from the length of the temperature-controlled section the aliquot size and the thermal expansion coefficient of the separation medium. In most cases, temperature differentials of at least 5 degrees Celsius, preferably at least 10 degrees Celsius, more preferably from about 10 to about 70 degrees Celsius, and still more preferably from about 20 to about 40 degrees Celsius, will be used.

A preferred method of performing the invention according to these embodiments is to allow the temperature drop to draw the separation medium inward at only one end of the capillary tube. In this manner, the sample aliquot will fill the entire volume difference resulting from contraction of the separation medium. This facilitates the calculation to determine the temperature and provides increased control over the sample volume. This may be achieved by any technique, readily apparent to those skilled in the art, for preventing or inhibiting liquid flow at the opposite end of the capillary. One such technique is to immerse the opposite end in a liquid of higher viscosity than the sample solution, and preferably both the sample solution and the separation medium, thereby presenting a greater resistance to flow at that end than at the sample loading end. A solution of a polymer, such as for example methyl cellulose, will serve effectively as the high viscosity liquid. Alternatively, the end of the tube may be closed by a dialysis membrane or a gel plug.

The temperature drop may be achieved by any conventional means, the various possibilities being readily apparent to those skilled in the art. Immersing the capillary in, or flooding its exterior with, a coolant liquid at the appropriate temperature is a most convenient way of achieving this result. This offers the further advantage of temperature control in the capillary at all times. Noting that electrophoretic migration velocities can vary as much as 2.5% with every 1° C. change in temperature close control of the temperature can significantly increase run reproducibility. Continuous cooling of the capillary tube also permits the use of higher voltages and thereby shorter run times, one of the most attractive features of capillary electrophoresis.

Once the sample aliquot is loaded onto the capillary column, the sample reservoir is removed and replaced with an appropriate buffer solution for electrophoresis. Care must be taken to prevent loss of the aliquot from the capillary during this exchange. This may be achieved by maintaining the temperature of the capillary at the temperature used for loading so that no expansion or contraction of the separation medium occurs. The system components may also be designed with appropriate channels and valve arrangements between different fluid reservoirs such that the switch can be made without disconnecting any parts.

Turning now to FIG. 1, a sketch of a somewhat primitive system is shown to illustrate the general concepts of the invention. A capillary tube of fused silica 11 is coiled around a support rod 12 inside a tray 13 filled with a heat transfer liquid of controlled temperature. The two ends 14, 15 of the capillary extend outside the tray 13 into external reservoirs 16, 17.

For sample loading, the capillary 11 is filled throughout its entire length with the separation medium, the outlet side reservoir 17 is filled with a buffer solution, preferably one containing a viscosity-raising solute such as methyl cellulose, and the inlet side reservoir 16 is filled with sample solution. The exposed ends 18, 19 of the capillary are immersed in the corresponding solutions. All media, including the heat transfer medium in the tray and the solutions in each of the two reservoirs, are at a starting temperature. With the media thus in place, sample loading is achieved by replacing the heat transfer liquid in the tray with a colder heat transfer medium, the temperature difference selected on the basis of the length of the capillary inside the tray, the capillary diameter and the thermal expansion coefficient of the separation medium inside the capillary, to achieve the desired volume contraction of the separation medium, drawing the same volume of sample in from the inlet side reservoir.

Once the system has equilibrated, the sample solution in the inlet side reservoir is replaced with buffer, and electrophoresis proceeds as the cold heat transfer medium is retained inside the tray 13. Detection in this embodiment is achieved by an ultraviolet beam 20 passing through the capillary at a point outside the cooling tray 13 at the side opposite the sample injection end. Other conventional methods of detection may also be used, such as for example fluorescence.

The embodiment shown in FIG. 2 includes a cartridge 30 which houses the capillary 31, and serves as a jacket or enclosure for the passage of a heat transfer fluid. Inlet and outlet ports 32, 33 for the heat transfer fluid permit continuous circulation of the fluid around the capillary exterior. An internal baffle 34 directs the fluid flow. The ends of the capillary are sealed into cone-shaped inlet and outlet ports 35, 36 which provide for communication of the capillary interior with the outside of the cartridge. These cone-shaped ports mate with similarly shaped connections 37, 38, 39 in fluid reservoir blocks for a pressure seal when the parts are combined in an appropriate support block.

The sample solution and the buffer solution which replaces the sample solution may be in different blocks 40, 41 as shown in the drawing, or combined into a single block in separate compartments with the connections controlled by valves, either manually or automatically operated. Alternatively, the selection between sample solution and electrode buffer may be controlled by a timed flushing mechanism. An outlet block 42 contains the buffer solution used at the outlet end of the capillary. Electrode connections 43, 44 are shown on each block. Detection is achieved by an ultraviolet beam passing through a window 46 which is aligned with the capillary at a point near the outlet port 38.

For those embodiments in which the temperature differential is applied to a bulb downstream of the capillary, a generalized representation is offered in FIG. 3. In this arrangement, the electrophoretic sample separation takes place in a portion 51 of the capillary shown to the right of the bulb 52. The sample is introduced at the right end 53 of the capillary, and the sample components migrate to the left during electrophoresis in the direction indicated by the arrow 54. The separated sample components are detected as they pass through a detection point 55, by a detection beam 56 such as a beam of ultraviolet light. The bulb 52 is enclosed or immersed in a jacket or cooling vessel 57 with inlet and outlet ports 58, 59 to permit the continuous flow of heat transfer fluid. Buffer reservoirs 60, 61 equipped with electrodes 62, 63 are included, as well as a sample reservoir 64 for sample loading, the sample reservoir being exchangeable with one of the buffer reservoirs 61 once the sample is loaded. In the Figure, the parts are arranged for sample loading. As one alternative to the arrangement shown, the left electrode 62 may be placed inside the bulb 52 rather than a separate reservoir.

In this embodiment, the parameters which govern the amount of liquid drawn into the capillary by the temperature differential applied to the bulb are the volume of the bulb, the temperature differential, and the coefficient of thermal expansion of the bulb contents. The bulb contents may be the same medium present in the separatory portion 51 of the capillary, or the two may be different. It will be most convenient to use a bulb filled with the same separation medium as in the capillary. In the arrangement shown, liquid will be drawn in at both sides of the bulb. As in the embodiments described above, however, the system may be adapted to draw liquid through the capillary on the right side only. The examples cited above will apply here as well, i.e., the use of a high viscosity liquid in the left buffer reservoir 60, or the use of a dialysis membrane or a gel plug on the left side of the bulb. In any event, the bulb must be filled with the thermally contractible medium.

With these considerations in mind, the volumetric capacity of the bulb is not critical and may vary widely. In most applications, it is contemplated that the bulb volume will range from about 1 mL to about 100 mL.

The temperature change is brought about by changing the temperature of the heat transfer fluid flowing through the jacket 57 surrounding the bulb. The amount of the change will of course be selected in accordance with the amount of liquid sought to be drawn into or through the separatory portion 51 of the capillary. A small temperature change will thus be sufficient to load a sample into the capillary, while a larger temperature change may be used to flush the entire separatory portion of the capillary with buffer solution.

In further embodiments of the invention, both a temperature-controlled bulb and a temperature-controlled capillary may be used at the same time, adding flexibility to the various procedures which can be followed and providing efficient temperature control of the capillary at all times.

The principle embodied in the bulb embodiments may be applied to a variety of systems. Automated systems designed for a series of separations performed in sequence will particularly benefit from the invention.

One example of such a system is shown diagrammatically in FIG. 4. As in the system described in FIG. 3, electrophoretic separation occurs in a capillary 70, and bulk movement inside the capillary is controlled by a jacketed bulb 71.

At the opposite end of the capillary 70 is a carousel 72 which contains wells 73 for sample and buffer. In the plan view of the carousel included in the Figure, the wells alternate between large wells 74 for buffer and small wells 75 for sample. The carousel surface is of a nonwettable material such as Teflon which permits the sample and buffer to form beads above the carousel surface when the wells are overfilled. When samples of very small volume are used, the carousel may be placed in a laboratory hood or other chamber to maintain an atmosphere saturated with water vapor to prevent reduction of the bead size due to evaporation.

The capillary and carousel are positioned relative to each other such that the open end 76 of the capillary extends into the bead which is in alignment with the capillary at any particular point in time. Electrodes 77, 78 are positioned appropriately, one of which 77 is associated with the buffer reservoirs, although not necessarily in direct contact. The direction of sample migration during electrophoresis in this arrangement is toward the right, as indicated by the arrow 79, and detection may be performed on-line by an appropriate beam 80. Other arrangements of these elements which serve the same function will readily come to mind among those skilled in the art.

To prepare for operation, the capillary 70 and bulb 71 are filled completely with buffer using conventional means such as a syringe, and the carousel wells are filled with alternating sample and buffer in sufficient amounts to form beads above the carousel surface. The carousel is then rotated to a position which places the capillary in contact with a sample bead and, with a shutoff valve 81 on the opposite side of the bulb closed, a small temperature drop is applied to the bulb causing a small sample volume to be withdrawn into the open end 76 of the capillary. While maintaining the bulb at the temperature to which it was lowered, the carousel is rotated to place a bead of buffer solution above one of the larger buffer wells 74 in contact with the capillary end, and an electric potential is applied across the electrodes to perform the electrophoresis.

Once the electrophoresis is complete, the capillary may be prepared for the next sample by lowering the temperature of the bulb 71 once again, this time by an amount to draw sufficient buffer through the capillary to flush it out entirely. The carousel is then rotated to the next sample well and the entire process repeated. The bulb temperature may be raised at any time without disturbing the capillary contents by opening the outer shutoff valve 81 to permit the discharge of fluid while closing an inner shutoff valve 82. As is readily apparent, capillary flushing may also be achieved by raising the bulb temperature to push buffer solution through the capillary in the opposite direction.

The present invention is applicable to the full range of types of electrophoretic separations which can be conducted in capillary tubes. Examples of such types are simple electrophoresis, discontinuous electrophoresis, displacement electrophoresis and isoelectric focusing.

The following example is offered for purposes of illustration, and is intended neither to define nor limit the invention in any manner.

EXAMPLE

An apparatus was assembled generally according to FIG. 1. The capillary was fused silica tubing of total length 210 mm and cooled length 140 mm. The internal diameter of the tubing was 0.05 mm. A buffer solution consisting of 0.1M Tris-acetic acid, pH 8.6 was used. The sample was a solution of 3,4-dimethoxybenzoic acid, prepared by dissolving 1 mg of 3,4-dimethoxybenzoic in 1 mL of the buffer, and diluting 1:10 with water.

The capillary tube was filled with the buffer solution and the tray was filled with water at room temperature (20° C.), and the right electrode vessel was filled with the buffer solution further containing 0.1% methyl cellulose. The left electrode vessel was filled with the sample solution. The water in the tray was then replaced by ice water (0° C.), resulting in the sample quickly being drawn into the tube to a length of 0.5 mm. This agreed with the calculated length of 0.5 mm. The sample solution in the left electrode was then replaced with buffer, and electrophoresis was commenced.

With the tubing and solutions described above, the calculated lengths of the loaded sample zone for given temperature drops and lengths of the cooled portion of the capillary are as follows:

| CALCULATED LENGTH OF APPLIED SAMPLE ZONE | | |
|---|---|---|
| Cooled Capillary Length (mm) | Temperature Drop (°C.) | Sample Zone Length (mm) |
| 200 | 20 | 0.72 |
| 200 | 30 | 1.1 |
| 200 | 40 | 1.4 |
| 300 | 20 | 1.1 |
| 300 | 30 | 1.6 |
| 300 | 40 | 2.2 |
| 400 | 20 | 1.44 |
| 400 | 30 | 1.62 |
| 400 | 40 | 2.88 |
| 500 | 20 | 1.80 |
| 500 | 30 | 2.70 |
| 500 | 40 | 3.60 |

The foregoing is offered for purposes of illustration. It will be readily apparent to those skilled in the art that numerous variations, modifications and substitutions may be made in the materials and procedures disclosed herein without departing from the spirit and scope of the invention.

What is claimed is:

1. A method for introducing a specified volume of liquid into a capillary tube in a capillary electrophoretic system, said capillary tube filled with an electrophoretic separation medium, said method comprising:
   (a) arranging said capillary tube such that one end of said capillary tube opens into a body of said liquid; and
   (b) with said capillary tube so arranged changing the temperature of a vessel filled with a fluid medium in fluid communication with said capillary tube by a preselected temperature differential, said fluid medium being one which is volumetrically responsive to temperature thereby causing a portion of said liquid to be transferred into said capillary tube, the magnitude of said temperature differential and the volume of said vessel being selected such that the amount of liquid thus transfered is equal to said specified volume.

2. A method in accordance with claim 1 in which said fluid medium and said electrophoretic separation medium are identical media.

3. A method in accordance with claim 1 in which said vessel is a portion of said capillary tube, and said fluid medium is the portion of said electrophoretic separation medium in said portion of said capillary tube.

4. A method in accordance with claim 1 in which said vessel is a portion of said capillary tube, and step (b) comprises lowering said temperature by at least about 5 degrees Celsius.

5. A method in accordance with claim 1 in which said vessel is a portion of said capillary tube, and step (b) comprises lowering said temperature by at least about 10 degrees Celsius.

6. A method in accordance with claim 1 in which said vessel is a portion of said capillary tube, and step (b) comprises lowering said temperature by about 10 to about 70 degrees Celsius.

7. A method in accordance with claim 1 in which said vessel is a portion of said capillary tube, and step (b) comprises lowering said temperature by about 20 to about 40 degrees Celsius.

8. A method in accordance with claim 1 in which said vessel is a portion of said capillary tube ranging from about 50 mm to about 2000 mm in length.

9. A method in accordance with claim 1 in which said vessel is a portion of said capillary tube ranging from about 100 mm to about 1000 mm in length.

10. A method in accordance with claim 1 in which said vessel is a portion of said capillary tube ranging from about 50 mm to about 2000 mm in length and said capillary tube has an inner diameter of about 10 to about 200 microns.

11. A method in accordance with claim 1 in which said vessel is a portion of said capillary tube ranging from about 50 mm to about 2000 mm in length and said capillary tube has an inner diameter of about 20 to about 100 microns.

12. A method in accordance with claim 1 in which said vessel is a portion of said capillary tube, and said temperature differential and the length of said portion of said capillary tube are selected such that said specified volume is from about 0.0003 to about 0.03 $\mu$L.

13. A method in accordance with claim 1 in which said vessel is a portion of said capillary tube, and said temperature differential and the length of said portion of said capillary tube are selected such that said specified volume is from about 0.0005 to about 0.005 $\mu$L.

14. A method in accordance with claim 1 in which said vessel is a portion of said capillary tube, and the end of said capillary tube opening into said liquid in step (a) is defined as an inlet end and the opposite end of said capillary tube is defined as an outlet end, and for the duration of step (b) said outlet end is immersed in an external liquid medium of sufficiently higher viscosity than said separation medium that any tendency to draw said external liquid medium into said capillary tube at said outlet end due to said lowering of temperature is suppressed.

15. A method in accordance with claim 1 in which said electrophoretic separation medium is a liquid.

16. A method in accordance with claim 1 in which said electrophoretic separation medium is a gel-free and polymer-free aqueous buffer solution.

17. A method for placing a specified volume of a liquid sample inside the inlet end of a capillary tube having inlet and outlet ends and an inner diameter of about 20 to about 100 microns, said capillary tube filled with a separation medium, for purposes of electrophoretic separation, said method comprising;
   (a) immersing said inlet end in a body of said liquid sample, and immersing said outlet end in an external liquid medium of substantially higher viscosity than both said liquid sample and said separation medium; and
   (b) passing a liquid heat exchange medium over the exterior of a central portion of said capillary tube measuring from about 100 to about 1000 mm in length, with said inlet and outlet ends so immersed, to lower the temperature of said central portion by a preselected temperature drop, thereby causing said liquid separation medium to contract, drawing a portion of said liquid sample into said capillary tube at said inlet end, said preselected temperature drop and the length of said central portion of said capillary tube being selected so that the amount of liquid sample thus drawn into said capillary tube is equal to said specified volume.

18. A method in accordance with claim 1 in which said vessel is a bulb adjoined to said capillary tube.

19. A method in accordance with claim 1 in which said vessel is a bulb adjoined to said capillary tube, the volume of said bulb ranging from about 1 mL to about 100 mL.

20. A method in accordance with claim 1 in which said vessel is a bulb adjoined to said capillary tube, and the volume of said bulb and the magnitude of said temperature differential are selected such that said specified volume is at least equal to the volume of said capillary tube.

21. A method of separating a mixture of species in a liquid solution into components in a capillary tube having inlet and outlet ends and filled with a separation medium at a starting temperature, said method comprising:
   (a) immersing said inlet end of said capillary tube in a body of said liquid solution;
   (b) lowering the temperature of at least a portion of said capillary tube below said starting temperature by a preselected temperature differential with said inlet end so immersed to cause said separation medium to contract and thereby draw a portion of said liquid solution into said inlet end of said capillary;
   (c) removing said inlet end of said capillary tube from said body of said liquid solution; and
   (d) imposing an electric potential across said capillary tube to cause electrophoresis of the portion of liquid solution thus drawn into said inlet end.

22. A method in accordance with claim 21 in which for the duration of step (b) said outlet end of said capillary tube is immersed in an external liquid medium of sufficiently higher viscosity than said separation medium that any tendency to draw said external liquid medium into said capillary tube at said outlet end due to said lowering of temperature is suppressed.

23. A method in accordance with claim 21 in which said preselected temperature differential and the length of said portion of said capillary tube lowered in temperature are selected such that the volume of said liquid solution thus drawn into said inlet end of said capillary tube is from about 0.0003 to about 0.03 $\mu$L.

24. A method in accordance with claim 21 in which said preselected temperature differential and the length of said portion of said capillary tube lowered in temperature are selected such that the volume of said liquid solution thus drawn into said inlet end of said capillary tube is from about 0.0005 to about 0.005 $\mu$L.

25. A method of separating a mixture of species in a sample solution into components in a capillary tube having inlet and outlet ends, said method comprising:
   (a) filling said capillary tube with a liquid separation medium at a starting temperature:
   (b) immersing said inlet end of said thus filled capillary tube in a body of said sample solution, and immersing said outlet end in an external liquid medium of substantially higher viscosity than both said sample solution and said liquid separation medium: and
   (c) passing a liquid heat exchange medium over the exterior of a central portion of said capillary tube measuring from about 100 to about 1000 mm in length, with said inlet and outlet ends so immersed, to lower the temperature of said central portion from said starting temperature by a preselected temperature differential, thereby causing said liquid separation medium to contract and a portion of said sample solution to be drawn into said capillary tube at said inlet end, said preselected temperature differential and the length of said central portion of said capillary tube being selected so that the amount of sample solution thus drawn into said capillary tube is equal to a preselected amount ranging from about 0.0003 to about 0.03 µL:

(d) removing said inlet end of said capillary tube from said body of said sample solution; and
(e) imposing an electric potential across said capillary tube to cause electrophoresis of the portion of said sample solution thus drawn into said inlet end.

* * * * *